United States Patent [19]
Daffer et al.

[11] Patent Number: 5,645,578
[45] Date of Patent: Jul. 8, 1997

[54] TOTAL THERAPY SAUNA BED SYSTEM

[75] Inventors: Steven J. Daffer, Edina; Roger E. Mitchell, Bloomington; Mirsaeed Rouzegar, Minneapolis, all of Minn.

[73] Assignee: Sybaritic, Inc., Edina, Minn.

[21] Appl. No.: 340,788

[22] Filed: Nov. 16, 1994

[51] Int. Cl.⁶ .................... A61N 5/00; A61H 1/00; A61G 10/00
[52] U.S. Cl. .................... 607/91; 607/88; 600/21; 600/27
[58] Field of Search ............ 601/23, 24, 46–56; 607/1, 2, 44, 45, 88, 90–95, 115; 600/21, 27

[56] References Cited

U.S. PATENT DOCUMENTS

| | | | |
|---|---|---|---|
| 3,014,477 | 12/1961 | Carlin | 128/1 |
| 3,556,088 | 1/1971 | Leonardini | 601/47 |
| 3,880,152 | 4/1975 | Nohmura | 601/47 |
| 4,055,170 | 10/1977 | Nohmura | 601/47 |
| 4,315,502 | 2/1982 | Gorges | 128/1 C |
| 4,640,266 | 2/1987 | Levy | 128/1 R |
| 4,858,609 | 8/1989 | Cole | 128/395 |
| 4,911,166 | 3/1990 | Leighton et al. | 128/380 |
| 5,046,494 | 9/1991 | Searfoss et al. | 128/395 |
| 5,047,006 | 9/1991 | Brandston et al. | 600/21 |
| 5,101,809 | 4/1992 | Daffer et al. | 128/33 |
| 5,101,810 | 4/1992 | Skille et al. | 607/47 |
| 5,113,852 | 5/1992 | Murtonen | 601/47 |
| 5,137,018 | 8/1992 | Chuprikov et al. | 128/395 |
| 5,259,380 | 11/1993 | Menoes et al. | 607/115 |
| 5,266,070 | 11/1993 | Hagiwara et al. | 600/27 |
| 5,292,345 | 3/1994 | Gerardo | 607/88 |
| 5,304,207 | 4/1994 | Stromer | 607/88 |
| 5,437,607 | 8/1995 | Taylor | 601/49 |
| 5,447,527 | 9/1995 | Waloman | 607/88 |

FOREIGN PATENT DOCUMENTS 1129308 10/1968 United Kingdom.

Primary Examiner—Lee S. Cohen
Assistant Examiner—Stephen Huang
Attorney, Agent, or Firm—Westman, Champlin & Kelly, P.A.

[57] ABSTRACT

A therapeutic device that provides light therapy in a sauna bed that has a hood that fits over the head of a person lying in a sauna bed. The hood has interior lights providing selected light intensity that simulates outdoor light at mid day and which directs and scatters the light in a manner substantially similar to the direction of light from natural sources onto the head of a user. A strobe light is also provided as well as selectable colored lights to permit the user to select a desired light regime.

19 Claims, 6 Drawing Sheets

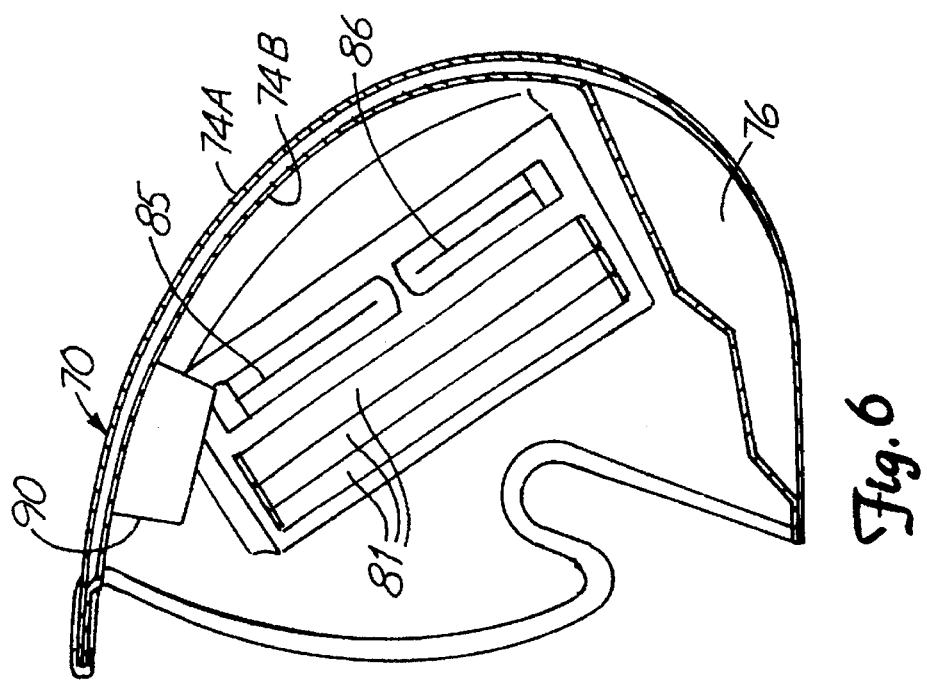
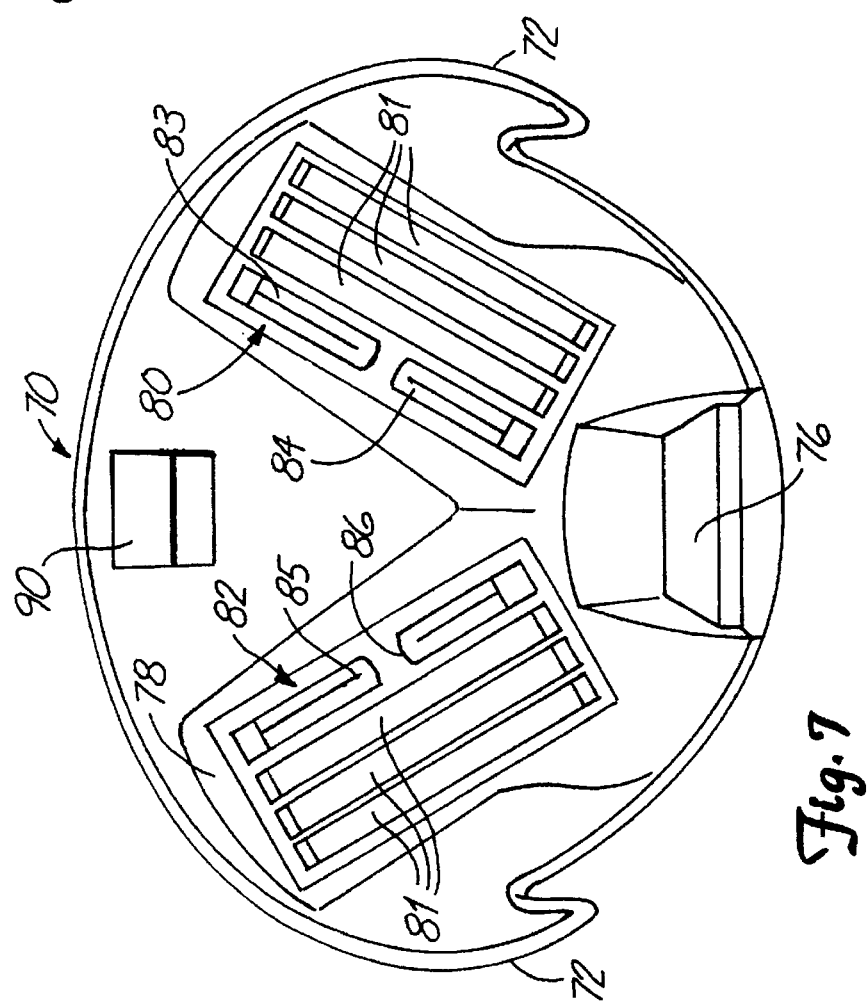

5,645,578

TOTAL THERAPY SAUNA BED SYSTEM

BACKGROUND OF THE INVENTION

The present invention relates to a therapeutic sauna bed system for providing light therapy to a user, by choosing a variety of colors of light for relaxation and other benefits.

The therapeutic benefits of utilizing light, as well as other relaxation techniques, including music, aroma, and vibration of the body has been known. Medical evidence indicates that health of people may be affected by exposure to light. A condition that is known as Seasonal Affective Disorder (SAD) has been recognized to induce more or less a depressive condition in persons on a periodic recurrence. These depression periods tend to occur during seasonal periods of low level and/or short duration of light.

Light therapy involves exposure to light for a regulated period of time which induces a feeling of well being. For example, U.S. Pat. No. 5,047,007 shows a personal integrating sphere that uses an illuminator that can be controlled for varying light sequences. It has also been found that a sense of well being can be induced by utilizing a vibrating type bed that is provided with heat, aroma, and music or pleasing sound and combining these conditions with light provides greater benefit than any of the treatments alone.

U.S. Pat. No. 5,266,070 shows a relaxation and refreshment apparatus that has a hood utilized on a chair for providing sound and other stimuli, including vibration and illumination of the interior of the hood.

A personal sauna bed that provides vibration, heat, and sound therapy is illustrated in U.S. Pat. No. 5,101,809. Combining light treatment for a person relaxed in such a sauna enhances enjoyment and benefits.

SUMMARY OF THE INVENTION

The present invention relates to a hood that can be pivoted from a retracted position to a usable position and which is attached to a head end of a vibratory sauna bed. The hood provides a support for lights of selected hues or colors and bright, full spectrum, white light in the sunlight range (high intensity) that is positioned so that it will strike a person lying in the sauna bed in the same manner as normal, bright mid-day sunlight, and provide for controllable light therapy.

In addition to the light that directly shines on the head of a user, coordinated or corresponding light is also provided on the interior of the sauna bed compartment. The interior controllable light hue or color is identical to the hood light color to provide benefits of exposure of the body to colored lights.

The present invention also provides a strobe light that can be selected to a particular frequency in synchronization with brain wave activity for inducing a relaxed state at the same time that the bright and/or colored light therapy is being utilized to provide for a controlled, highly integrated therapy arrangement using heat, vibration, aroma, sound and light.

By permitting the user to select the color of the light, as well as the frequency of the strobe light, a light condition that is beneficial and most enjoyable to the user can be provided under the user's control.

BRIEF DESCRIPTION OF THE DRAWINGS

FIG. 6 is a sectional view of the hood assembly only, showing a mounting device for light boxes on the side of the hood, and also the mounting for a strobe light;

FIG. 7 is a front elevational view of the hood shown in FIG. 6;

DETAILED DESCRIPTION OF THE PREFERRED EMBODIMENTS

Figure 1:
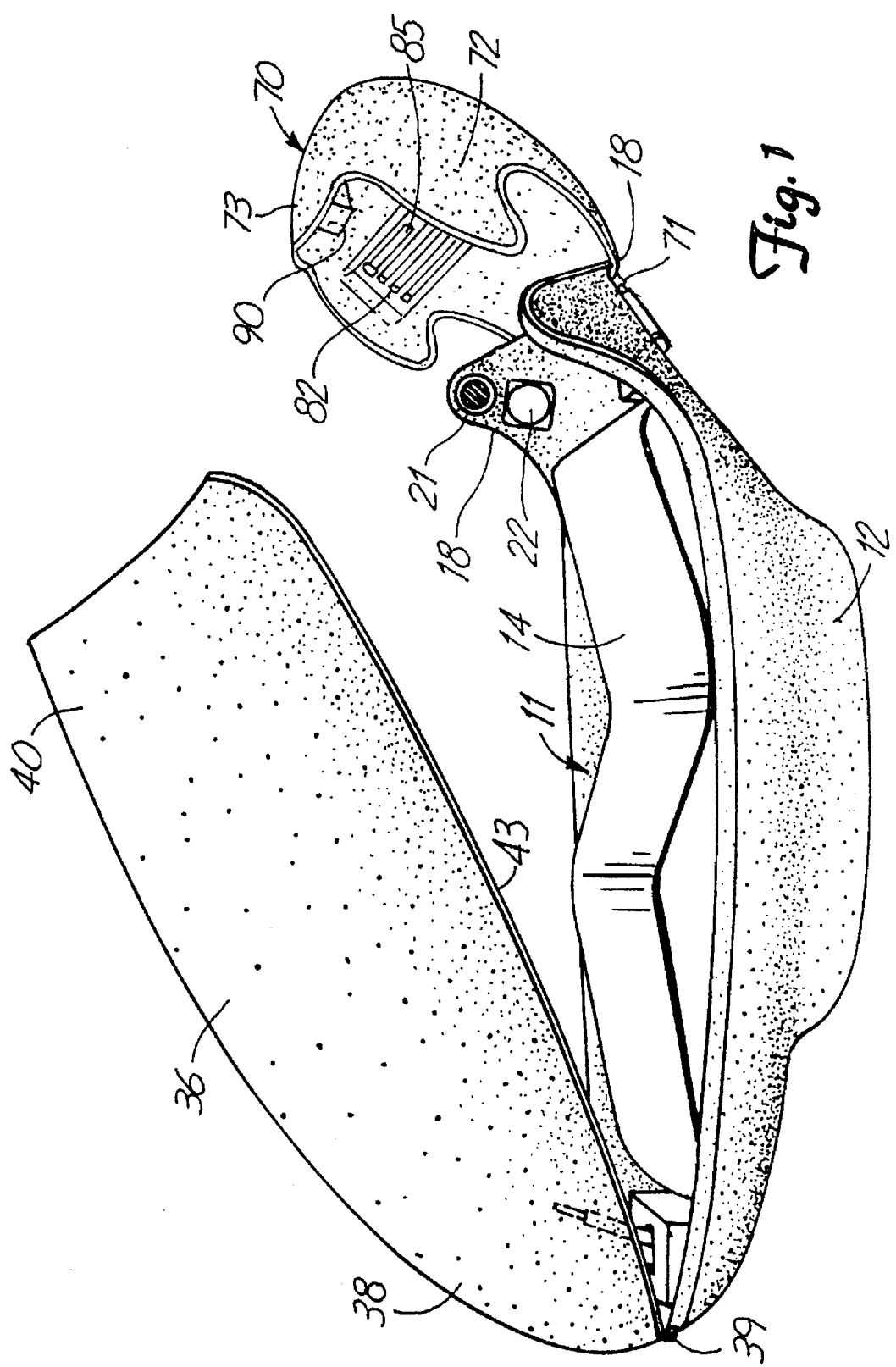
FIG. 1 is a perspective view of a sauna bed having a light therapy hood made according to the present invention installed thereon.

The light therapy apparatus illustrated generally at 10 comprises a vibratory sauna bed assembly 11 including a supporting pedestal 12. A blower and heated air flow duct system indicated generally at 13 for blowing uniformly directed, heated, recirculated air over a person in the sauna. The pedestal 12 supports a bed or cushion 14, and an individual shown in dotted lines in FIG. 2 at 16 is supported on the bed 14. The construction is shown essentially in U.S. Pat. No. 5,101,809. As shown at a head portion 17, the sauna bed has wings 18 that come up around the sides of a head of a user and a support wall 18A is used for supporting the head of the user on a suitable pillow or pad. The body compartment shown at 19 will support the entire body except for the head of the user. Wing members 18 are hollow, and provide space for air flow ducts so that cool air can be directed from an inlet, through a fan 28 and compartment 29 and through vents 21, as desired to blow across the sides of the face of the user. The fan 28 can be controlled by a suitable switch.

Suitable speakers for sound therapy indicated at 22 are also provided, and provide stereo music or other sounds to enhance the pleasurable experience.

The air directed through the duct system 13 can be scented with a suitable aroma from a liquid essence pump (diffuser or nebulizer) 25. One or more of the electric operated aroma or scented liquid sprayers can be used. The diffuser or nebulizers are mounted underneath the bed 14. Therefore the aroma is circulated uniformly along the openings that are provided alongside the bed 14 and into the entire chamber 19, as well as along and through the head opening. The aromatic essences are uniformly distributed along the body of the user. The scent is released inside the body chamber 19 and wafts out along the head opening to the head of the user. An aroma or scent dispenser pump can also be provided in cool air compartment 29 if desired, as shown.

The fresh air through vents 21 will tend to counter the flow of heated air from the body compartment 19. The blower duct system 13 provides uniformly heated, downwardly directed recirculating air. The duct system 13 is mounted on the cover member 36 of the sauna. The cover member 36 has a foot end 38 and a head end 40 which defines the body compartment 19. The cover member 36 is hinged to the pedestal 12 at the foot end 38 and extends substantially along the entire length of the bed 14. The hinge is shown at 39 in FIG. 2.

A head end opening 42 is provided for the head of a user to extend out from the body compartment 19.

Figure 8:
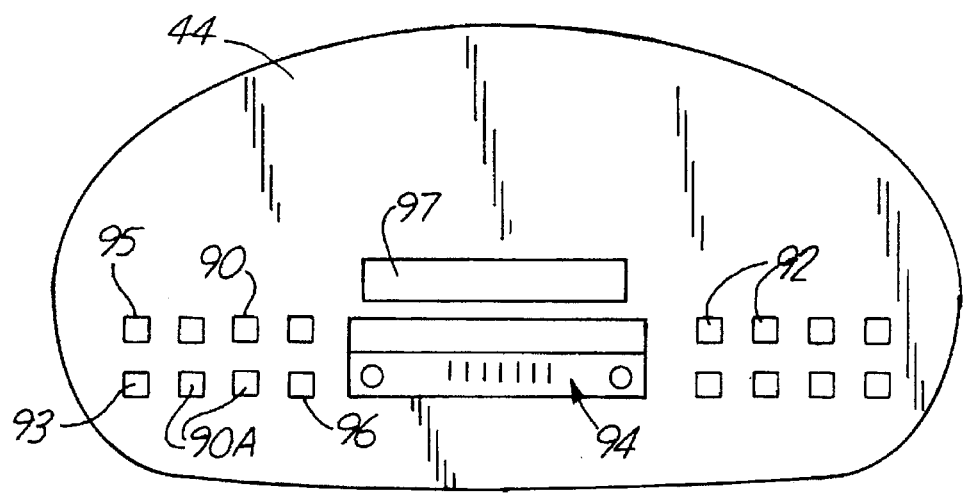
FIG. 8 is an elevational view of a typical control panel used with the present invention.
Figure 4:
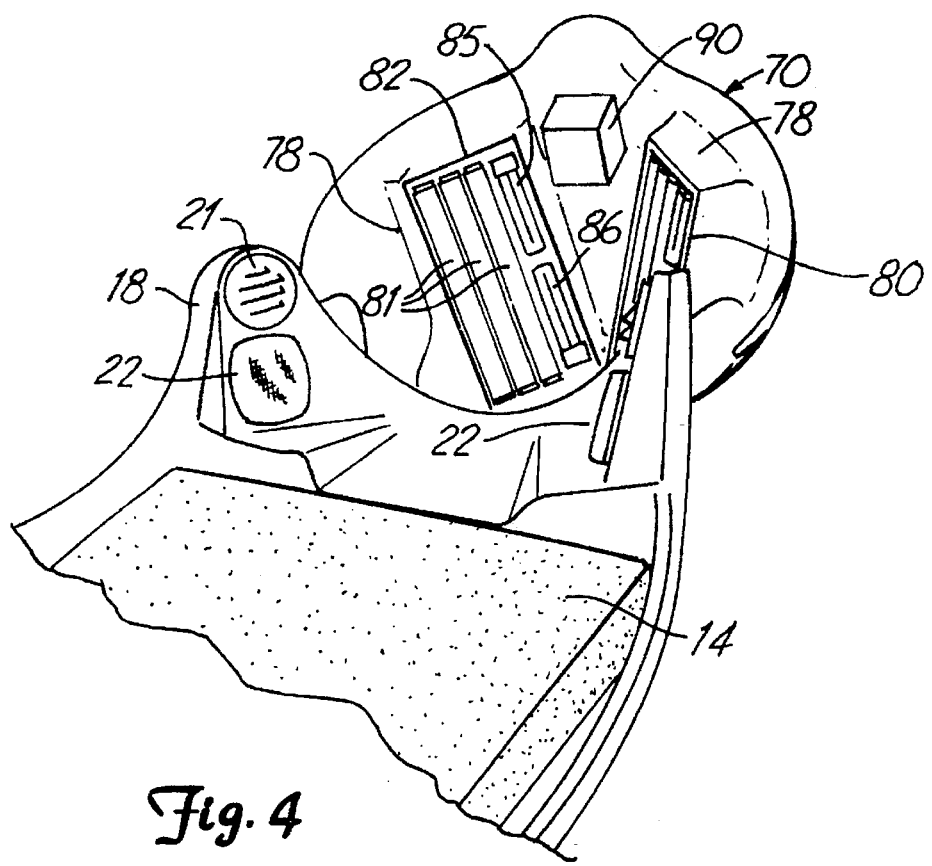
FIG. 4 is a further perspective view of the hood of FIG. 3 in an open position, and illustrating the supports for lights on the interior of the hood.

A resilient seal along the lower edges of the panel indicated generally at 43 in FIG. 1 can be utilized for sealing this compartment. Control panel 44 is provided and is accessible to the user and can have suitable controls as will be explained, for temperature, vibration, sound volume, and light in accordance with the present invention. Control switches can be on the face of the control panel of the unit as shown in FIG. 8.

Blower duct system 13 intakes air through inlets 48, and then the blower will blow the air as indicated by the arrow 49 across a heater 47 and out through a blower outlet 50 and up into an interior duct 52. Outlet openings 56 are provided along sides of the duct 52 to direct air as indicated by the arrows 53 downwardly over the body. This construction also is shown in U.S. Pat. No. 5,101,809. Heated or cooled air driven by the blower or fan 60 will flow through the duct chamber 52, and provide an even air flow over the body of the user. The outlet openings 56 are provided with deflector vane covers if desired. The cover 36 can be counter balanced with a pneumatic cylinder if desired, as well.

Electric vibrators shown at 66 can be mounted onto the bed 14, and the bed is supported on suitable elastomeric members shown at 67 to walls 68 of the base 12, so that the bed will vibrate when the electric vibrator 66 are energized. The vibrators can be placed at desired locations for obtaining a therapeutic or pleasurable vibration during use. The vibration intensity and frequency can be changed with suitable controls, as desired.

Figure 2:
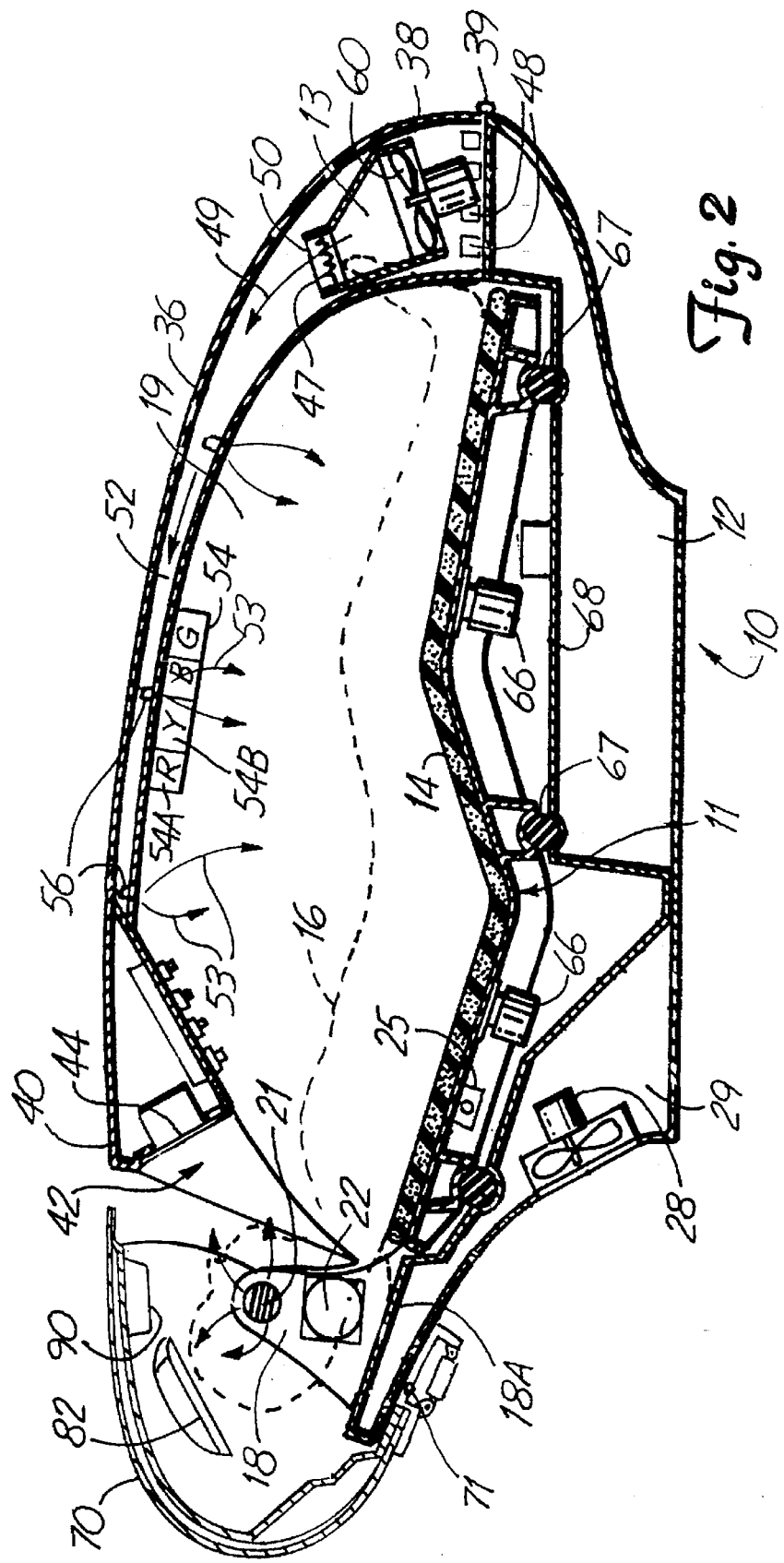
FIG. 2 is a longitudinal sectional view of the sauna bed of FIG. 1 to show the internal arrangement of the parts with the light therapy hood in a closed usable position.
Figure 3:
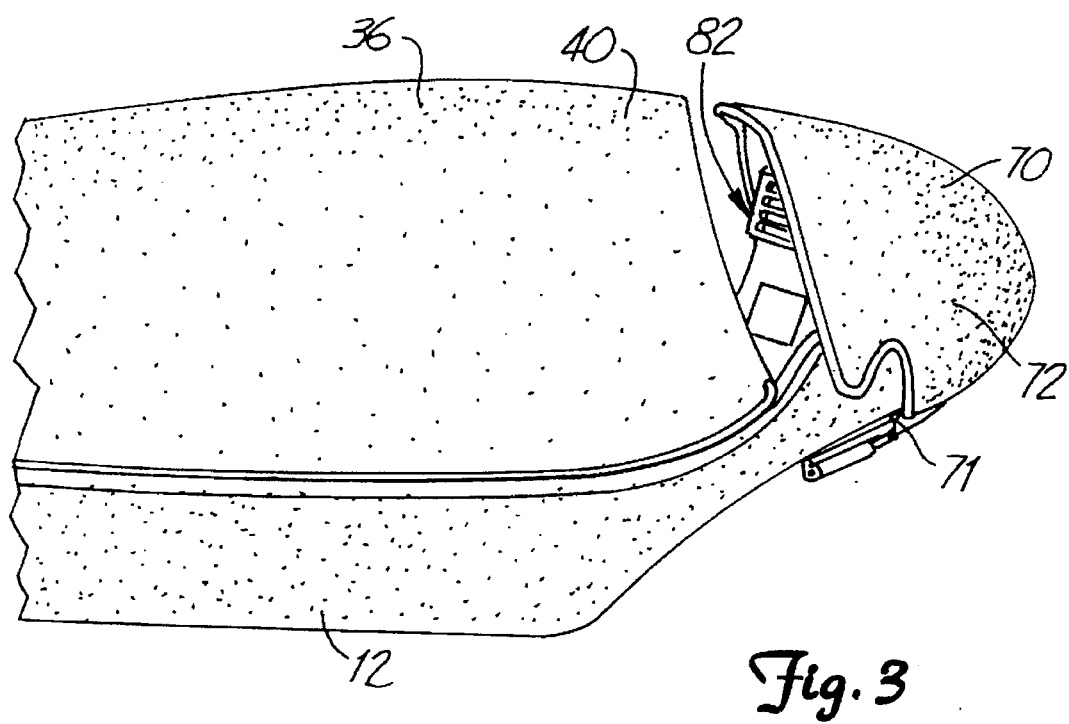
FIG. 3 is a fragmentary side elevational view of the device of FIG. 1 showing the light therapy hood in a closed position for use by a recipient of light therapy.

An environment hood 70 is mounted with a suitable hinge 72 to the head end 18 of the base 12, and can be hinged from an open position shown at FIG. 1 to a closed position shown in FIGS. 2 and 3. The hood 70 is smoothly formed to a pair of side wall portions 72 that extend downwardly from an upper wall portion 73 in a curved form (see FIGS. 6 and 7) and as shown, the wall can have spaced portions 74A and 74B to provide an interior space for passing electric wires and the like into a chamber 76 that is formed to house needed components. Control lines are passed back to the control panel 44 for controlling various functions. The hood 70 has a pair of interior support platforms 78 formed on opposite sides of the hood. The platforms 78 in turn support light boxes of housings 80 and 82, on the opposite sides of the hood. The light boxes 80 and 82 contain high intensity white lights 81. These are generally three short fluorescent lights in each light box that will give up to 9,000 lux total light intensity, with all lamps illuminated. Individual colored lamps shown generally at 83 for red, 84 for yellow, 85 for green and 86 for blue are also monitored in the light boxes. The positioning of the colored lamps can be at any desired location, inside the respective light boxes. Usually, two colored lights are positioned in each light box. The individual color lights can be controlled for separate lighting or a selected combination of light, or all of the lights can be on at once.

A strobe light 90 is mounted at the top interior of the hood 70, so that when the hood is closed, generally as shown in FIG. 2, the strobe light will be slightly ahead of and above the eyes of the person 16 lying on the bed 14. That means the strobe light 90 will be directly in view of a person lying in the personal sauna. The strobe light has a diffuser cover to provide a general flash of light rather than an intense direct light from a bulb.

Control panel 44 shown in FIG. 8 has a touch control switch indicated at 92 that provide for selection of the individual lights, or colors, or a combination of all of them. This control panel also has vibrator controls 91, and strobe light on-off and frequency controls 93.

The control panel also supports a CD player-radio 94 and aroma dispense controls 95 for the aroma pumps. The white light bulbs provide a very high or intense light level, and as shown, this light comes in from the sides and slightly above the head of the user, to simulate very closely the direction of sunlight at mid day. Vibrator controls 90 and fan and heater controls 90A are also provided. A user prompt and manage display screen 97 aid in selecting the appropriate function and operation.

Figure 9:
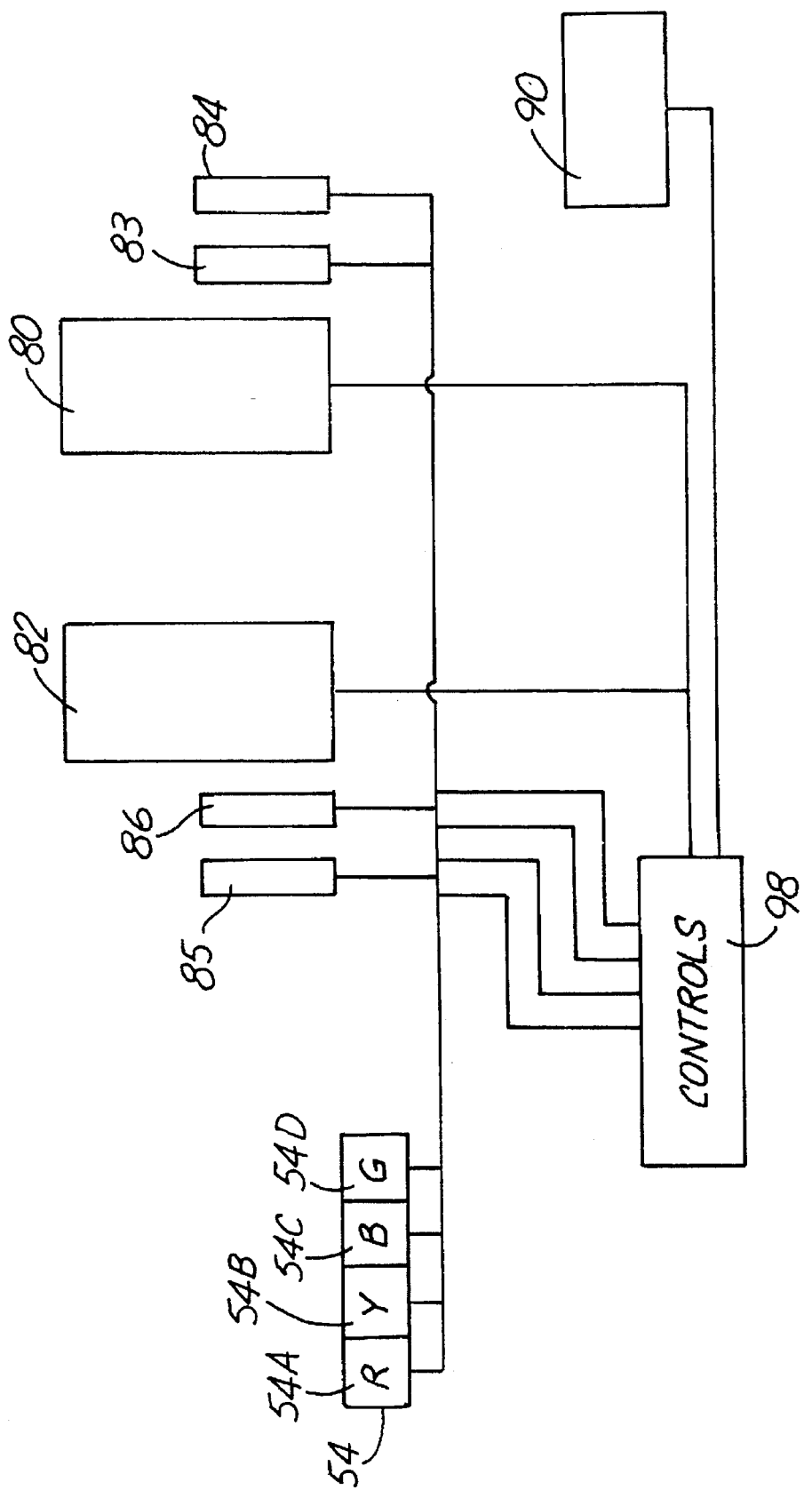
FIG. 9 is a schematic diagram of the light controls used with the device of the present invention.

In FIG. 9, controls are indicated in unit 98 for the individual lights. The controls are selected to provide the ability to turn lights in the light boxes 80 and 82 on or off and the time "on" also can be set with a timer 96. The white lights 81 are indicated by separate blocks in FIG. 9, and the light box 54 for the interior chamber 19 is shown divided up into red, yellow, blue and green sections 54A, 54B, 54C and 54D. Each color of light is connected in parallel with the same color individual light 83, 84, 85 and 86 in the hood 70 and thus the same color interior and hood lights are on at the same time.

The strobe light 90 is controlled as to frequency by controls 98, so that the frequency of the strobe light 90 can be adjusted to suit the user. The strobe light frequency, as stated coincides with brain wave activity. For an "Alpha" state of general relaxation, 5 Hz to 12 Hz has been found beneficial. The "Theta" state of relaxation haw been found frequency of 1–5 Hz. 12 Hz and up provide "Beta" state relaxation. Thus, adjustments between 1 Hz and 12 Hz for strobe light frequency is preferred.

Figure 5:
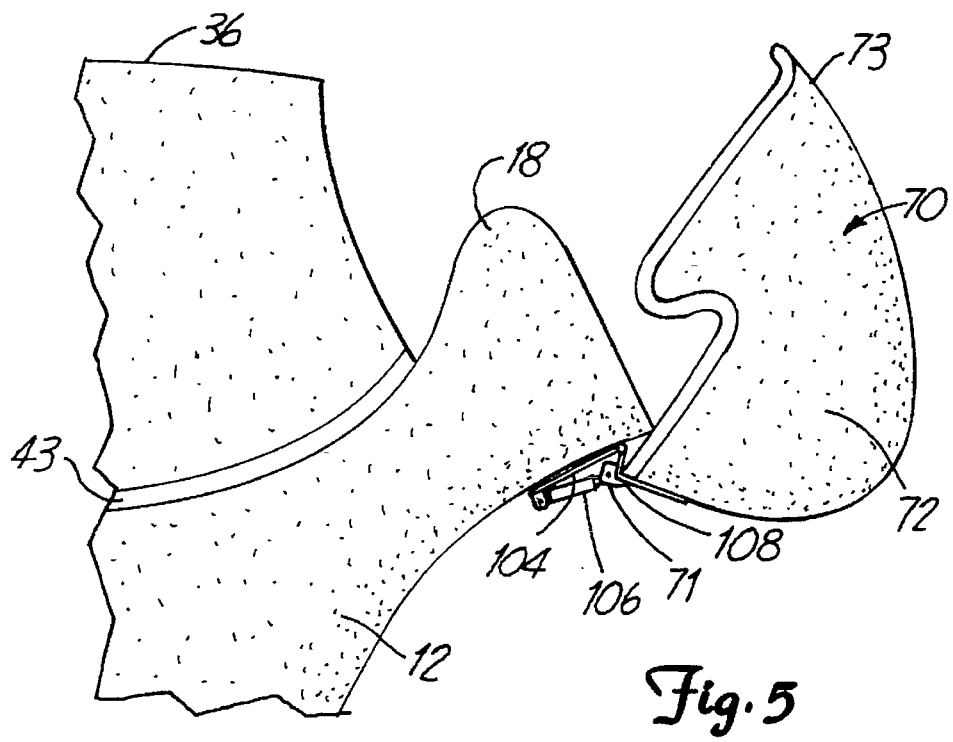
FIG. 5 is a side elevational view of the device of FIG. 3 with the hood in an open position and illustrating the use of a shock absorbing and controlled force hinge arrangement.

The light therapy module is in the hood 70 that comes up over the head of the user, and once a person lies in the body compartment 19 and closes the cover 36, the hood 70 can be pivoted up on the hinge assembly 71. As shown in FIG. 5, the hinge assembly 71 includes a support base 104 that mounts a prepressurized pneumatic or air cylinder 106 that in turn has a rod that attaches to a hinge section 108 mounted on the hood 70, to provide for a counter balancing of the hood so that it can be raised and lowered easily and gently.

The hood 70 is raised up over the head of the user for use. The control panel 44 then is manipulated to provide for the necessary light therapy, music, as well as heat and vibration all at the same time. The white light uses fluorescent bulbs that are of balanced intensity so that they are very close to the outdoor sunlight, and provide about 9,000 lux. The light is scattered over the top and sides of the head of the person much like at mid day. The user can select from red, green, blue or yellow lights as additional inputs on the programmed unit. The light boxes actually go about half way alongside the head so that there is a feeling like the outdoors. The frequency of the strobe light can be adjusted by the user to a desired frequency.

The coordinating lights on the interior of the cover 36 provide that the entire body is bathed in the same color light as that which is being projected onto the head that is either the red, green, blue or yellow light combination. The strobe light provides pulsating light at relatively low frequency. The head, vibration and aroma added to the selected light therapy combine to provide an increased effectiveness of relaxation. This is further heightened by the full body reclining and support on bed 14. Music or pleasing sound is provided through the speakers, by suitable controls as is known, and the air flow can also be controlled.

The interior light box provides for the same color light that is selected at the hood lights. Light from the interior, visible at the head opening still has overall light coordination.

Although the present invention has been described with reference to preferred embodiments, workers skilled in the art will recognize that changes may be made in form and detail without departing from the spirit and scope of the invention.

What is claimed is:

1. A therapy module comprising a hood member adapted to overlie a substantial portion of a rear and a top of a head of a user and having an opening in a direction in a field of view of the user, and at least one light box within the hood member having a selectively energized high intensity white light source positioned to project light from the light source directly downwardly across eyes of a user to illuminate a head of a user sufficiently to simulate positioning and intensity of natural mid day light projected directly from the white light source without reflection.

2. The module of claim 1 and a plurality of secondary lights in the hood member providing at least two additional colors selected from the group consisting of red, blue, yellow and green, and positioned to direct a selected colored light unto the user from a position adjacent to the white light source.

3. The module of claim 2 and a strobe light mounted within the hood member in a position to direct light into a face of a user, said strobe light providing a pulsing light of a selected frequency of intensity for therapeutic use.

4. The module of claim 3 and at least one speaker for therapeutic sound adjacent the hood.

5. The module of claim 4 and at least one duct for providing fresh air to a position adjacent the hood member.

6. The device of claim 3 and control means for providing an adjustable rate of lighting of the strobe light.

7. The module of claim 1 wherein the module includes a generally horizontally orientated support bed, and an enclosure for surrounding a substantial portion of the support bed to provide air flow over the support bed while the light source is illuminated.

8. The module of claim 7 and a light source within the enclosure, said light source having individual secondary colored lights selected from the group of red, yellow, blue and green, and means for connecting the individual secondary lights in the hood member with corresponding colored sources within the enclosure.

9. The module of claim 7, and an aroma carrying liquid injector for injecting a desired aroma into the enclosure.

10. A therapy module comprising a hood member adapted to overlying a substantial portion of a head of a user and defining an interior space and having an opening through which a user can see with the hood member in use, a first source of white light mounted in the interior space, a second light source of a selected color within the interior space, and a control to select at least one light source to illuminate the interior of the hood member, the light sources both being within the interior space and adjacent a side of the hood member and spaced from the opening of the hood member to directly project light onto a face of a user from the respective light source without depending on reflection.

11. The therapy module of claim 10 wherein the white light source is a high intensity white light source positioned to direct light directly across eyes of a user to simulate positioning and intensity of natural light at mid day.

12. The therapy module of claim 11 and a white strobe light mounted in the hood in a position adjacent the opening to the hood member wherein said strobe light provides a pulsing light of a selected frequency between 1 Hz and 12 Hz.

13. The therapy module of claim 10 and wherein the second light source comprises a plurality of secondary lights having at least two additional colors selected from the group consisting of red, blue, yellow and green, and positioned adjacent to the white light source.

14. The module of claim 13 and a white strobe light mounted in the hood in a position adjacent the opening to the hood, said strobe light providing a pulsing light of a selected frequency.

15. The module of claim 14 and a support bed, a cover forming an enclosure for a substantial portion of a body of a user, the hood member being pivotally mounted to a head end of the bed such that a user lying on the bed is at least partially enclosed by the hood member with the hood member in a closed position.

16. The module of claim 15 and a heated air duct in the enclosure providing a flow of heated air therein, a dispenser for dispensing scented material into the enclosure, a vibrator for vibrating the bed, and an interior light inside the enclosure providing colored light to the interior of the enclosure that is identical to the colored light provided to the interior of the hood member from the second source.

17. The module of claim 16, wherein said interior light provides light selected from the group consisting of red, yellow, blue and green, and controls for selecting activation of the secondary lights and interior light which automatically match color of the interior light and secondary lights for adjusting the frequency of the strobe light.

18. The therapy module and support bed of claim 15 wherein a mounting of the hood member to the head end of the bed provides for pivoting the hood member to a position wherein a person lying on the bed can lie in place and pivot the hood member to its position overlying a substantial portion of a head of the user.

19. A therapy module comprising a hood member adapted to overlie a substantial portion of a rear and top of a head of a user and having an opening in a direction in a field of view of the user, and at least one light box within the hood member having a selectively energized high intensity white light source positioned to provide direct light projected directly downwardly across eyes of a user to stimulate positioning and intensity of natural mid day light directly from the white light source without substantial reflection, and a strobe light mounted within the hood member in a position to direct light into a face of the user, said strobe light providing a pulsing light of a selected frequency and intensity for therapeutic use.

* * * * *

UNITED STATES PATENT AND TRADEMARK OFFICE
CERTIFICATE OF CORRECTION

PATENT NO. : 5,645,578
DATED : July 8, 1997
INVENTOR(S) : Daffer et al.

It is certified that error appears in the above-indentified patent and that said Letters Patent is hereby corrected as shown below:

Column 6, line 3, after "light" insert --downwardly--.

Column 6, line 49, delete "stimulate" and insert --simulate--.

Signed and Sealed this

Thirtieth Day of December, 1997

Attest:

BRUCE LEHMAN

Attesting Officer

Commissioner of Patents and Trademarks